(12) United States Patent
Li (10) Patent No.: US 10,993,776 B2
(45) Date of Patent: May 4, 2021

(54) CONSOLE FOR OPERATING ACTUATING MECHANISM

(71) Applicant: CHENGDU BORNS MEDICAL ROBOTICS INC., Sichuan (CN)

(72) Inventor: Zhiqiang Li, Sichuan (CN)

(73) Assignee: CHENGDU BORNS MEDICAL ROBOTICS INC., Chengdu (CN)

( * ) Notice: Subject to any disclaimer, the term of this patent is extended or adjusted under 35 U.S.C. 154(b) by 0 days.

(21) Appl. No.: 16/750,004

(22) Filed: Jan. 23, 2020

(65) Prior Publication Data

US 2020/0155255 A1 May 21, 2020

Related U.S. Application Data

(63) Continuation of application No. PCT/CN2018/097467, filed on Jul. 27, 2018.

(30) Foreign Application Priority Data

Jul. 31, 2017 (CN) .......................... 201710643884.6

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/74* (2016.02); *A61B 17/062* (2013.01); *A61B 17/28* (2013.01);
(Continued)

(58) Field of Classification Search
CPC combination set(s) only.
See application file for complete search history.

(56) References Cited

U.S. PATENT DOCUMENTS 7,822,466 B2 * 10/2010 Stoianovici ............ A61B 34/30
600/427
2010/0225209 A1 9/2010 Goldberg et al.

FOREIGN PATENT DOCUMENTS

CN 105188590 A 12/2015
CN 105816243 A 8/2016
(Continued)

OTHER PUBLICATIONS

International Search Report, Written Opinion, and Claims (Translation) for PCT International App. Serial No. PCT/CN2018/097467; dated Oct. 8, 2018 (9 pages).

*Primary Examiner* — Scott Luan
(74) *Attorney, Agent, or Firm* — Ulmer and Berne, LLP (57) ABSTRACT

Disclosed is a console for operating an actuating mechanism, relating to the technical filed of automatic control, and being for use in resolving the technical problem of shift of a controller under the influence of gravity. The console for operating an actuating mechanism includes a controller and a support base. The controller is constrained in both the longitudinal direction and the vertical direction, so that connection between the controller and the support base is tight and reliable, and no displacement would occur in any of three directions (i.e., the longitudinal direction, the horizontal direction, and the vertical direction). Thus, the phenomenon that position information given by the controller is inaccurate due to shift of the controller under the influence of the gravity after long-term usage can be avoided, thereby removing the factors affecting success of surgery, and ensuring the success rate of the surgery.

11 Claims, 8 Drawing Sheets

(51) Int. Cl.
 *A61B 17/062* (2006.01)
 *A61B 17/28* (2006.01)
 *A61B 17/3201* (2006.01)
 *A61B 17/3211* (2006.01)

(52) U.S. Cl.
 CPC ....... *A61B 17/3201* (2013.01); *A61B 17/3211* (2013.01)

(56) References Cited

FOREIGN PATENT DOCUMENTS

CN 105832488 A 8/2016
CN 107361849 A 11/2017

\* cited by examiner

CONSOLE FOR OPERATING ACTUATING MECHANISM

CROSS-REFERENCE TO RELATED APPLICATIONS

This application is a continuation application of PCT patent application No. PCT/CN2018/097467 filed on Jul. 27, 2018, which claims the priority of Chinese patent application No. 201710643884.6, entitled "Console for operating actuating mechanism" and filed on Jul. 31, 2017. The entirety of the above applications is incorporated herein by reference.

FIELD OF THE INVENTION

The present disclosure relates to the technical field of automatic control, and in particular, to a console of robot, automobiles, and aircraft for operating an actuating mechanism.

BACKGROUND OF THE INVENTION

Minimally invasive surgery is surgery performed by doctors with the help of endoscopes and minimally invasive surgical instruments. This type of surgery requires high operating accuracy and action stability. Moreover, the surgery takes a long time, which will make a doctor feel very tired and may increase the doctor's hand tremor, fatigue, and muscle and nerve feedback, resulting in inaccurate operation, increasing patient suffering, and reducing the success rate of the surgery. Under such circumstances, surgical robots have emerged, and they can provide visual guidance or monitoring service functions during surgery and provide a robot integrated system assisting doctors to complete surgical operations of high quality. Surgical robots have improved the quality of surgery, can overcome the defects of traditional minimally invasive surgery, widen the scope of minimally invasive surgery, and can also perform surgical simulation.

At present, mature surgical robots generally adopt a master-slave operating manner. Namely, an independent master operating end is used to control actions of a slave-end robot. In order to facilitate operation by a doctor, a controller (master controller) on a console is generally arranged in a longitudinal direction, i.e., perpendicular to a panel direction of the console. However, the existing controllers and consoles are only connected in the longitudinal direction. After long-time usage, the controller will shift under the influence of gravity, resulting in inaccurate position information given by the controller and affecting the success rate of the surgery.

SUMMARY OF THE INVENTION

The present disclosure provides a console for operating an actuating mechanism, for use in solving the technical problem in the existing art of shift of a controller under the influence of gravity.

A console for operating an actuating mechanism provided in the present disclosure includes a controller for operating an actuating mechanism, and a support base for fixing the controller.

The support base includes a panel extending in a vertical direction, and an observation platform located below the panel and extending in a horizontal direction.

The controller includes a connecting member, which is connected to the panel and the observation platform respectively.

In one embodiment, the connecting member includes a frustum, of which an axis is perpendicular to a plane where the panel is located.

The panel is provided with a tapered hole, and the frustum is provided in the tapered hole.

In one embodiment, the connecting member further includes an annular pressure plate fixedly connected to the observation platform, and a fixing collar is provided between the annular pressure plate and the observation platform.

An axis of the annular pressure plate and an axis of an observation hole on the observation platform coincide with each other.

In one embodiment, an inner ring of the annular pressure plate is provided with a mounting groove, and an outer wall of the frustum is connected to a connecting block provided in the mounting groove.

The tapered hole is provided with a first opening portion, and the connecting block is provided in the first opening portion.

In one embodiment, an outer ring of the annular pressure plate is provided with an extended portion extending in a radial direction of the annular pressure plate, a second opening portion is provided between the panel and the observation platform, and the extended portion is provided in the second opening portion.

The first opening portion and the second opening portion are in communication with each other.

In one embodiment, the controller further includes a control handle provided on the frustum, the control handle being a handheld or clamping handle.

In one embodiment, the support base is configured to lift up and down on a chassis, a bottom of the chassis is provided with pedals, and the observation hole is used for exposing the pedals to a doctor's field of view.

In one embodiment, the support base further includes a mounting beam and a cantilever, one end of the cantilever being connected to the panel, and the other end of the cantilever being connected to the mounting beam.

In one embodiment, an elbow support platform is further provided on the mounting beam, the elbow support platform and the mounting beam each being configured as an arc-shaped structure, of which an outer side is bent in a direction away from the panel.

The elbow support platform and the mounting beam have a similar degree of bending.

In one embodiment, the panel is provided with an emergency operation button, an indicator light, and a speaker.

Compared with the existing art, the present disclosure has the following advantages. The connecting member in the controller is connected to the panel in the support base, so that the controller is subject to a constraint force in the longitudinal direction. In addition, the connecting member is also connected to the observation platform in the support base, so that the controller is subject to a constraint force in the vertical direction. Namely, the controller is constrained in both the longitudinal direction and the vertical direction, so that connection between the controller and the support base is tight and reliable, and no displacement would occur in any of three directions (i.e., the longitudinal direction, the horizontal direction, and the vertical direction). Thus, the phenomenon that position information given by the controller is inaccurate due to shift of the controller under the influence of gravity after long-term usage can be avoided, thereby removing the factors affecting success of surgery, and ensuring the success rate of the surgery.

BRIEF DESCRIPTION OF THE DRAWINGS

The present disclosure will be described in more detail below based on the embodiments and with reference to the accompanying drawings.

REFERENCE SIGNS

1—controller; 2—elbow support platform; 3—support base; 4—chassis 1; 11—connecting member; 12—control handle; 31—panel; 33—mounting beam; 32—cantilever; 34—observation platform; 35—first opening portion; 36—second opening portion; 41—pedal; 111—frustum; 112—annular pressure plate; 113—mounting groove; 114—connecting block; 115—extended portion; 116—fixing collar; 121—clamp plate; 122—grip portion; 123—trigger; 311—tapered hole; 312—emergency operation button; 313—indicator light; 314—speaker

DETAILED DESCRIPTION OF THE EMBODIMENTS

The present disclosure will be explained in detail below with reference to the accompanying drawings.

Figure 1:
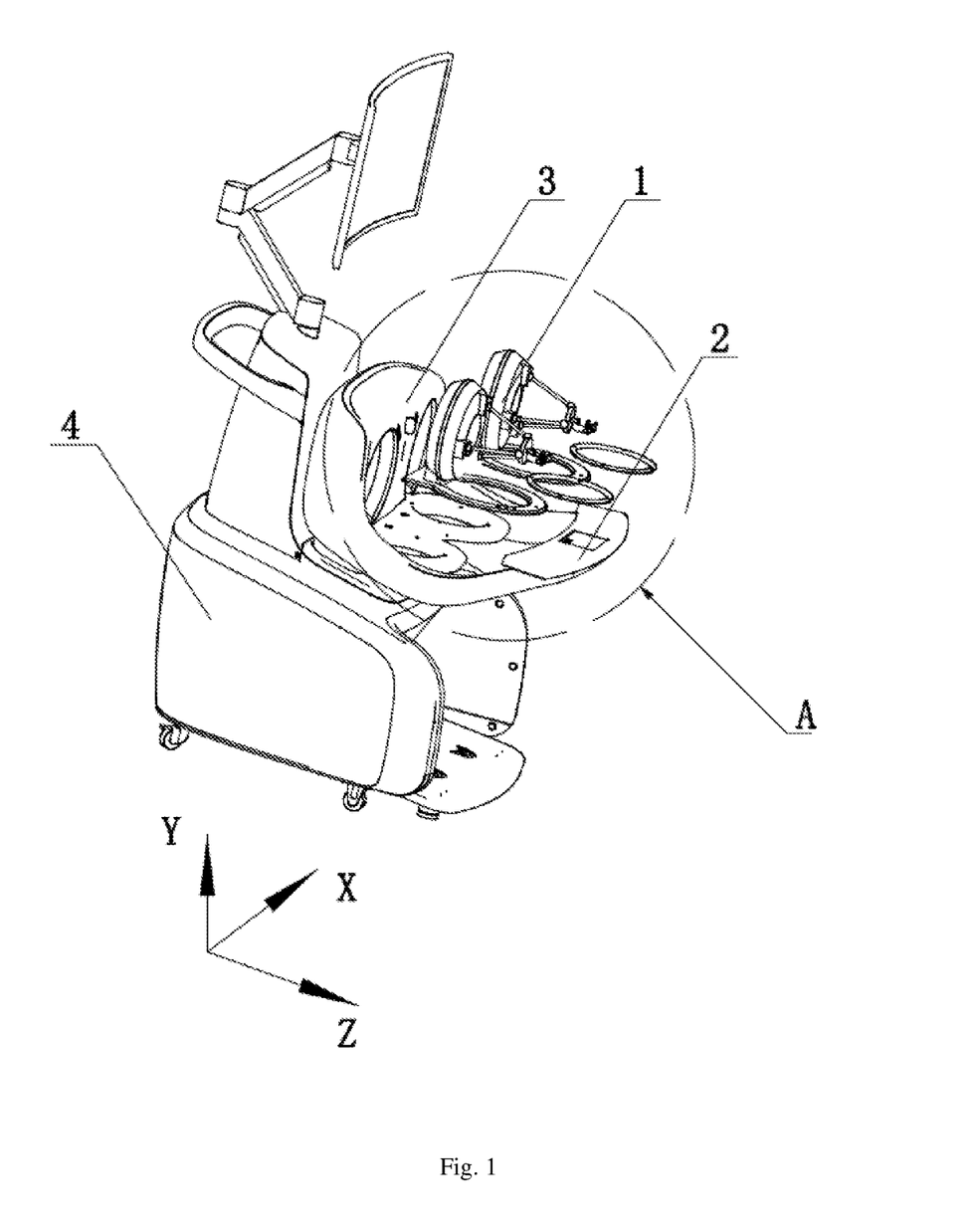
FIG. 1 is a perspective view of a structure of a console for operating an actuating mechanism in a first embodiment of the present disclosure.

First, directions in the present disclosure are defined as follows. As shown in FIG. 1, a console is erected in a right-handed rectangular coordinate system, a vertical direction (an extending direction of a panel) is a Y-axis direction, a horizontal direction (an extending direction of a mounting beam) is an X-axis direction, and a longitudinal direction (an extending direction of a slide rail) is a Z-axis direction. A doctor stands in the Y-axis direction. When the doctor performs an operation, his/her face is directly facing the front of the console.

Figure 6:
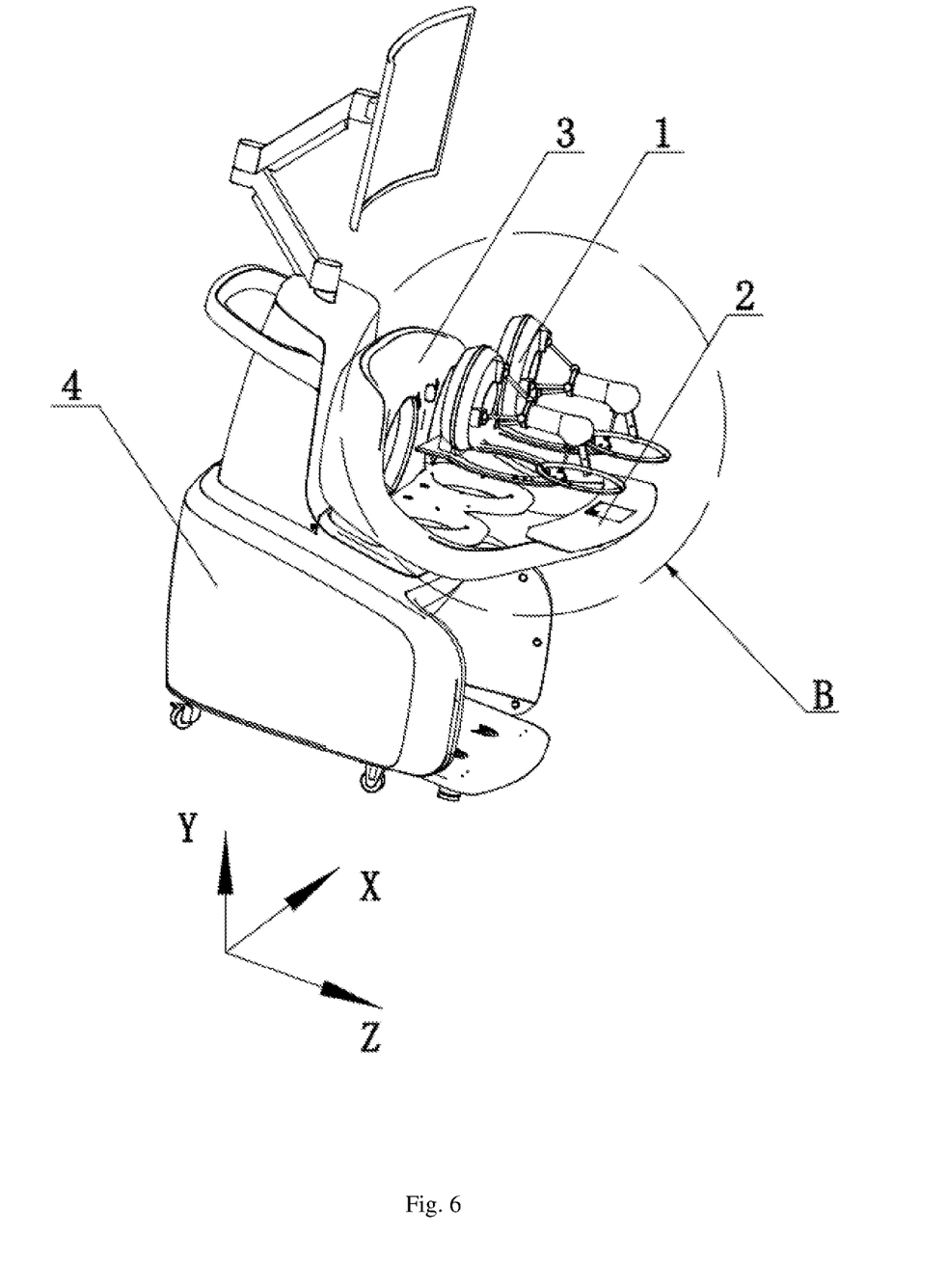
FIG. 6 is a perspective view of a structure of a console for operating an actuating mechanism in a second embodiment of the present disclosure.

As shown in FIGS. 1 and 6, the embodiments of the present disclosure provide a console for operating an actuating mechanism, the console including a controller 1 for operating an actuating mechanism, and a support base 3 for fixing the controller 1.

Figure 3:
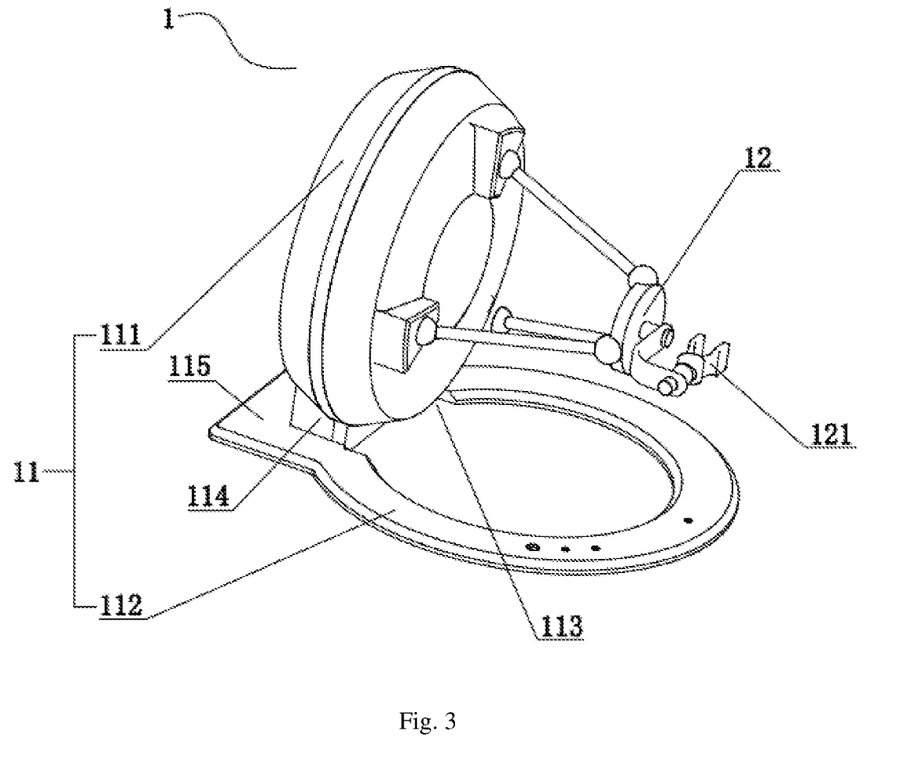
FIG. 3 is a perspective view of a structure of a controller shown in FIG. 1.
Figure 4:
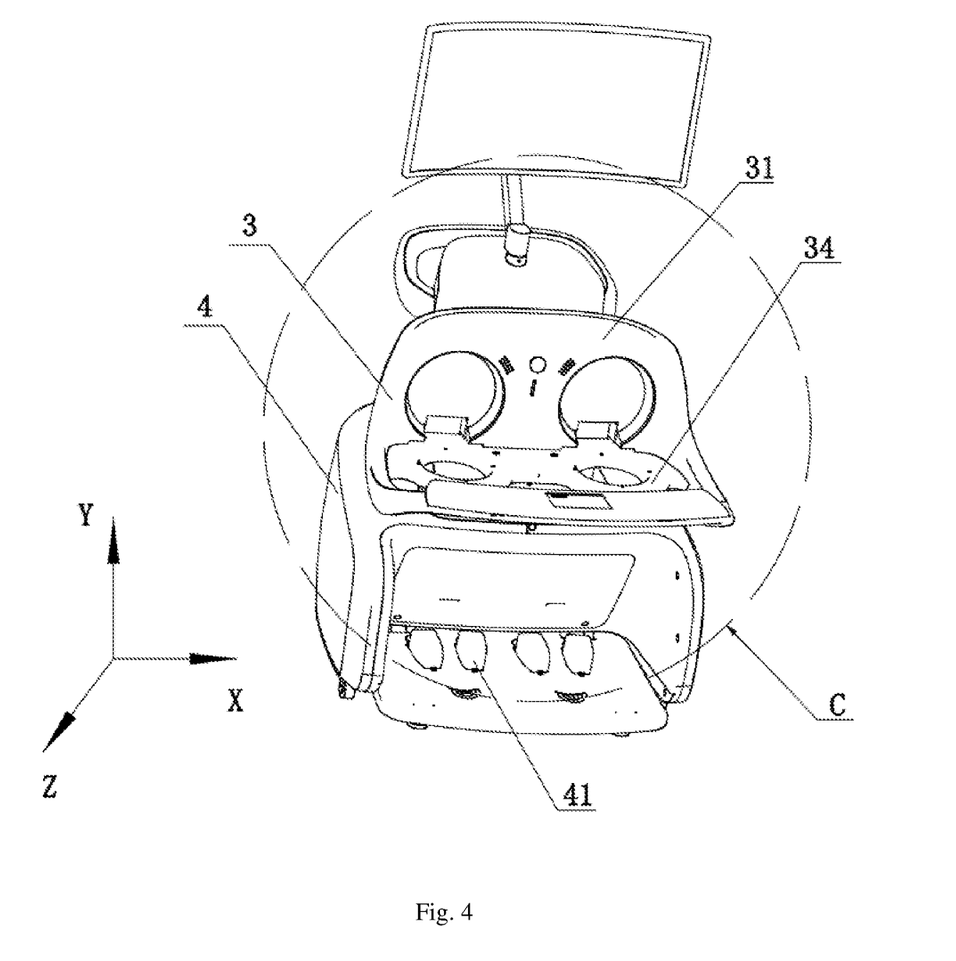
FIG. 4 is a perspective view of a structure of a support base shown in FIG. 1.

The support base 3 includes a panel 31 extending in the vertical direction, and an observation platform 34 located below the panel 31 and extending in the horizontal direction. Namely, an extending direction of the panel 31 is perpendicular to an extending direction of the observation platform 34. The controller 1 includes a connecting member 11, which is connected to the panel 31 and the observation platform 34 respectively. As shown in FIG. 3 and FIG. 4 (the controller 1 is not shown in FIG. 4), the connecting member 11 is connected to the panel 31, so that the connecting member 11 is subject to a constraint force in the longitudinal direction (Z-axis direction). In addition, the connecting member 11 is connected to the observation platform 34, so that the connecting member 11 is subjected to a constraint force in the vertical direction (Y-axis direction).

Further, the connecting member 11 includes a frustum 111, of which an axis is perpendicular to a plane where the panel 31 is located. The panel 31 is provided with a tapered hole 311, and the frustum 111 is provided in the tapered hole 311. A diameter of one end of the frustum 111 near the observation platform 34 is larger than a diameter of the other end of the frustum 111, so that the frustum 111 can be conveniently placed in the tapered hole 311.

In addition, in order to make the tapered hole 311 constrain the frustum 111, the taper of the tapered hole 311 is the same as that of the frustum 111. When the frustum 111 is placed in the tapered hole 311, an outer wall of the frustum 111 completely fits an inner wall of the tapered hole 311.

By providing the frustum 111 in the tapered hole 311, the connecting member 11 is subject to constraint forces in the horizontal direction (X-axis direction) and the vertical direction (Y-axis direction). The controller 1 is now completely constrained in three directions (i.e., the longitudinal direction, the horizontal direction, and the vertical direction), so that connection between the controller 1 and the support base 3 is tight and reliable, and no displacement would occur in the three directions. Thus, the phenomenon that position information given by the controller is inaccurate due to shift of the controller under the influence of gravity after long-term usage can be avoided, thereby removing the factors affecting success of surgery, and ensuring the success rate of the surgery.

Figure 2:
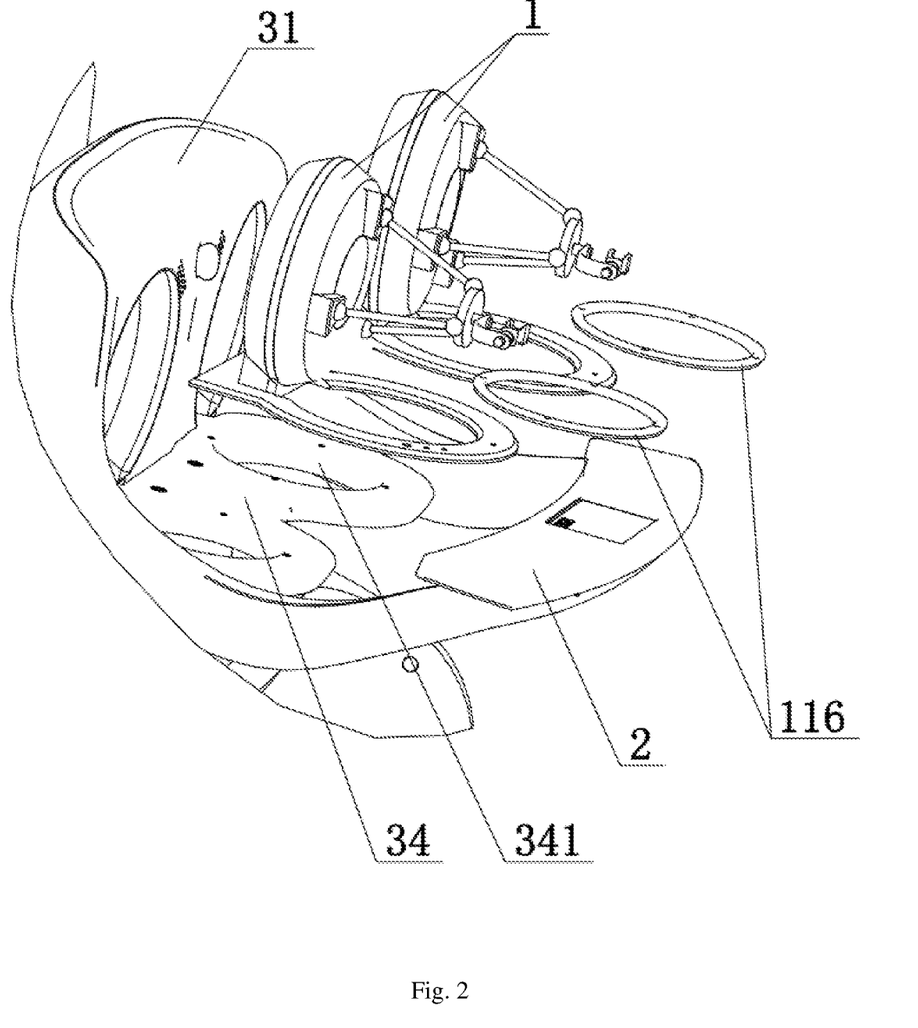
FIG. 2 is an enlarged view of an area A shown in FIG. 1.
Figure 8:
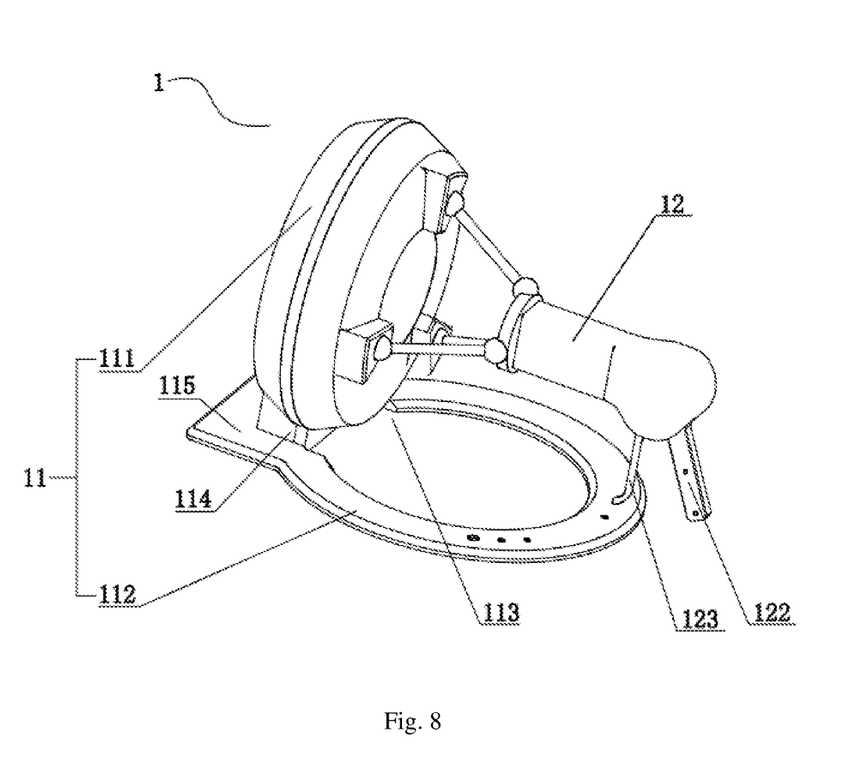
FIG. 8 is a perspective view of a structure of a controller shown in FIG. 6.

As shown in FIGS. 2, 3 and 8, the connecting member 11 further includes an annular pressure plate 112 fixedly connected to the observation platform 34. A fixing collar 116 is provided between the annular pressure plate 112 and the observation platform 34. The fixing collar 116 is made of a metal material so as to ensure its abrasion resistance.

Figure 7:
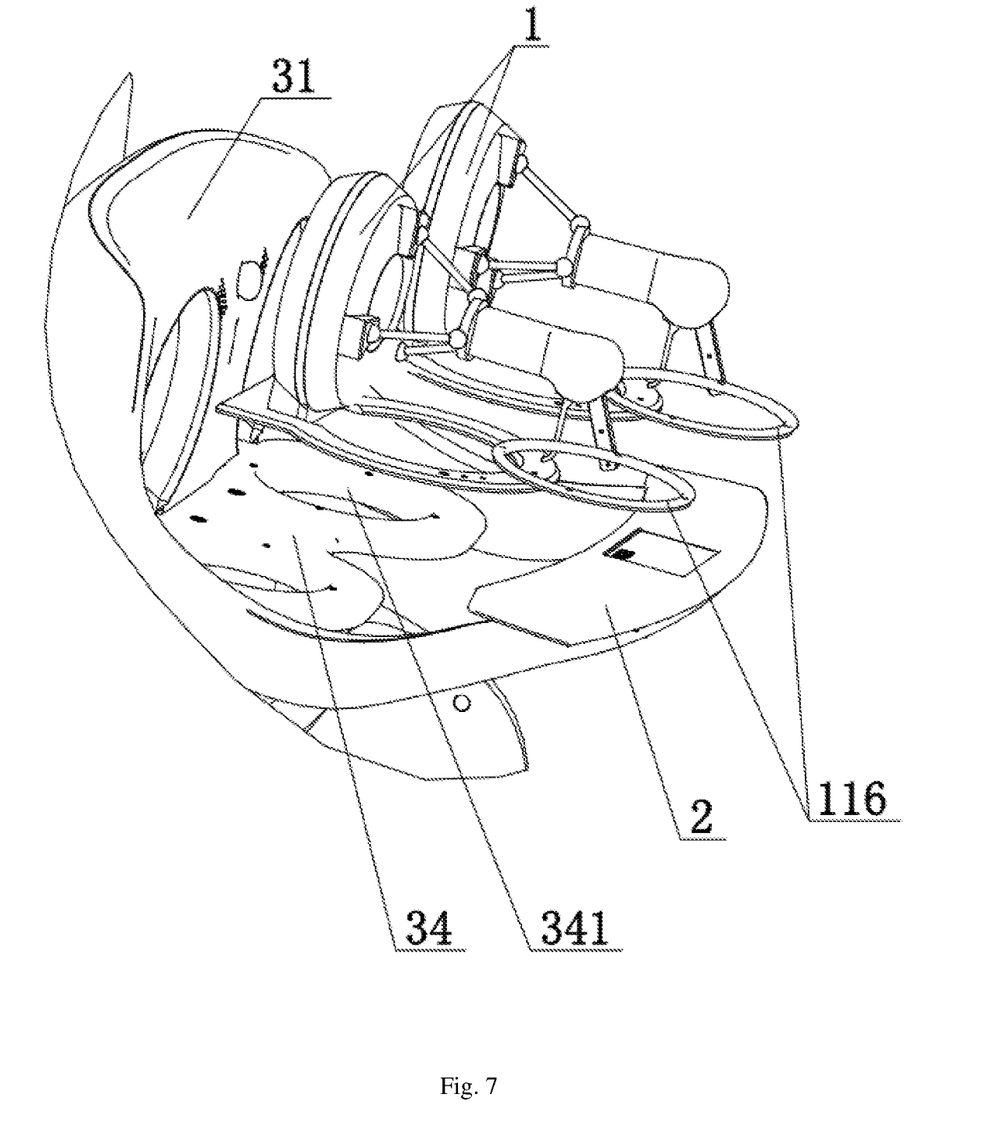
FIG. 7 is an enlarged view of an area B shown in FIG. 6.

In addition, an axis of the annular pressure plate 112 and an axis of an observation hole 341 on the observation platform 34 coincide with each other. As shown in FIGS. 2 and 7, an axis direction of the observation hole 341 is parallel to the Y-axis direction, and the doctor can therefore monitor, through the observation hole 341, the components (such as the pedals 41 etc.) controlled by his/her feet. Therefore, on the one hand, the annular pressure plate 112 can be fixedly connected to the observation platform, and on the other hand, the annular pressure plate 112 would not block the doctor's sight because a middle portion of the annular pressure plate 112 is provided with a hole.

The frustum 111 and the annular pressure plate 112 are connected in the following manner. An inner ring of the annular pressure plate 112 is provided with a mounting groove 113 that extends in a radial direction of the annular pressure plate 112, and an outer wall of the frustum 111 is connected to a connecting block 114 provided in the mounting groove 113 (as shown in FIGS. 3 and 8).

Figure 5:
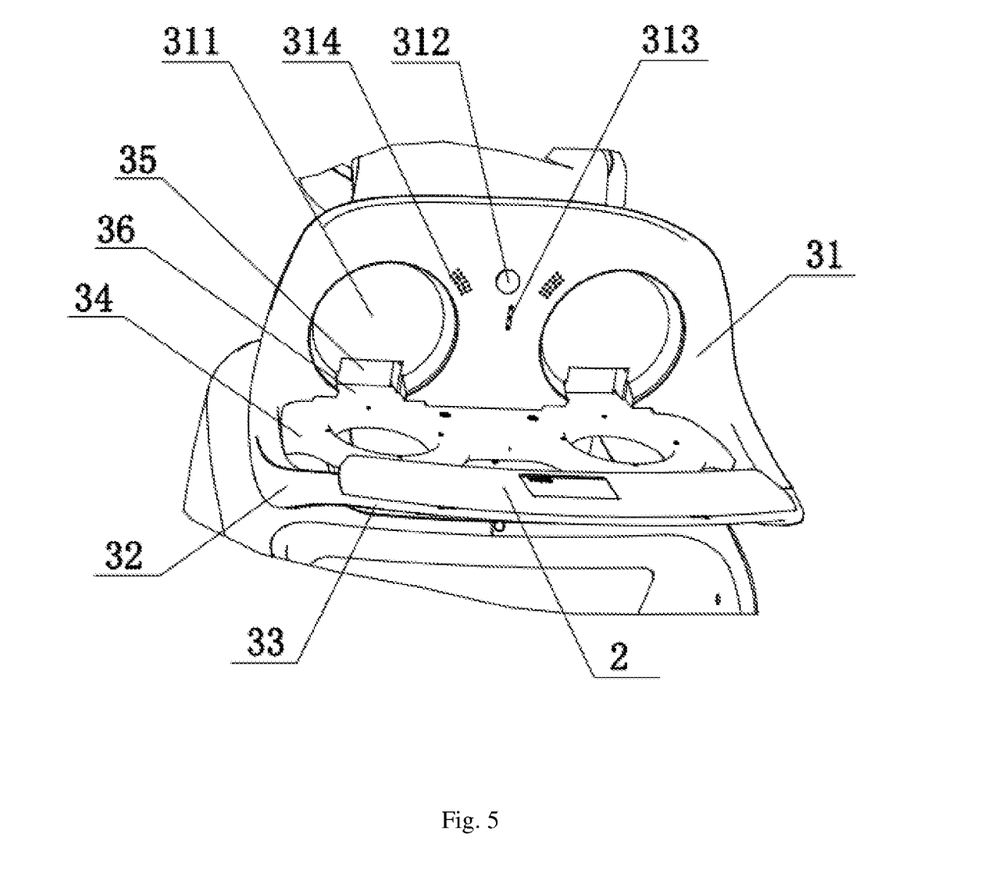
FIG. 5 is an enlarged view of an area C shown in FIG. 4.

In order to avoid interference between the tapered hole 311 and the connecting block 114, the tapered hole 311 is provided with a first opening portion 35, and the connecting block 114 is provided in the first opening portion 35 (as shown in FIG. 3 and FIG. 5).

Further, in order to prevent an axial runout of the annular pressure plate 112, an outer ring of the annular pressure plate 112 is provided with an extended portion 115 extending in a radial direction of the annular pressure plate 112, a second opening portion 36 is provided between the panel 31 and the observation platform 34, and the extended portion 115 is provided in the second opening portion 36. The first opening portion 35 and the second opening portion 36 are in communication with each other.

Specific steps of connecting the controller 1 to the support base 3 are as follows.

In a first step, the fixing collar 116 is placed on the observation platform 34, and the annular pressure plate 112 is placed on the observation platform 34.

In a second step, the controller 1 is moved in the longitudinal direction until the frustum 111 extends into the tapered hole 311, the axes of the annular pressure plate 112, fixing collar 116 and observation hole 341 coincide with one another, the extended portion 115 extends into the second opening portion 36, and the connecting block 114 is placed in the first opening portion 35.

In a third step, the annular pressure plate 112, the fixing collar 116, and the observation platform 34 are fixedly connected by means of threads.

In a first embodiment of the present disclosure, as shown in FIG. 3, the controller 1 further includes a control handle 12 provided on the frustum 111, the control handle 12 being a clamping handle.

Further, a tail end of the control handle 12 is a clamp plate 121. The clamp plate 121 can vividly reflect a shape of an end effector so that the doctor can truly feel feedback information during surgery, thereby making the control handle have a good operability.

In addition, the tail end of the control handle 12 also can be configured as a scalpel, a pair of surgical scissors, a needle holder, a pair of dissecting forceps and the like according to application objects, and is not repeatedly described herein.

In a second embodiment of the present disclosure, as shown in FIG. 8, the controller 1 further includes a control handle 12 provided on the frustum 111, the control handle, 12, being a handheld handle.

Further, the tail end of the control handle, 12, is provided with a grip portion 122 and a trigger 123. During surgery, the doctor holds the grip portion 122 with his/her hand and pulls the trigger 123 to change a position state of the control handle. In this process, the doctor has a good grip feeling so that the control handle, 12, has a good operability.

On the basis of the above two embodiments, the support base 3 is configured to lift up and down on a chassis 4. A lifting bracket can be provided at a bottom of the support base 3, and a position of the support base 3 in the vertical direction can be adjusted by means of the lifting bracket so that the support base 3 can be suitable for doctors of different heights.

As shown in FIG. 4 (the controller 1 is not shown in FIG. 4), pedals 41 are provided at a bottom of the chassis 4, and the observation hole 341 is used for exposing the pedals 41 to the doctor's field of view.

The support base 3 further includes a mounting beam 33 and a cantilever 32. One end of the cantilever 32 is connected to the panel 31, and the other end thereof is connected to the mounting beam 33. There are two cantilevers 32, and they are arranged symmetrically about a center of the support base 3 so as to fully adapt to the structure of the human body.

An elbow support platform 2 is further provided on the mounting beam 33, the elbow support platform 2 and the mounting beam 33 each being configured as an arc-shaped structure, of which an outer side is bent in a direction away from the panel 31. The elbow support platform 2 and the mounting beam 33 have a same degree of bending. Since the mounting beam 33 supports the elbow support platform 2 and does not affect body parts of the doctor, the mounting beam 33 has a structure substantially the same as that of the elbow support platform 2, but is slightly smaller than the elbow support platform 2, so that the elbow support platform 2 can completely cover the mounting beam 33 without affecting the support of the mounting beam 33 to the elbow support platform 2.

Fully taking into account such a situation that there is a certain distance between the body and the elbow joint after placing the arm on the elbow support platform 2, the elbow support platform 2 is bent toward a positive direction of a Z axis shown in FIG. 1. Therefore, such an arc-shaped bending structure can prevent the arm from being stressed by the body and keep the arm in a relaxed posture for surgery.

In addition, the elbow support platform 2 with the arc-shaped structure can also maintain a certain aesthetic appearance.

The elbow support platform 2 is slidably connected to the mounting beam 33 so that a position of the elbow support platform 2 can be adjusted in the Z-axis direction so as to adapt to doctors of different heights.

The panel 31 is provided with an emergency operation button 312, an indicator light 313, and a speaker 314. An interior of the panel 31 is provided with a cavity so as to reduce the weight of the console and provide mounting space for the emergency operation button 312, the indicator light 313, and the speaker 314.

Although the present disclosure has been described with reference to the preferred embodiments, various modifications can be made to the present disclosure and the components therein can be replaced with equivalents without departing from the scope of the present disclosure. In particular, as long as there is no structural conflict, the technical features mentioned in the embodiments can be combined in any manner. The present disclosure is not limited to the specific embodiments disclosed herein, but includes all technical solutions falling within the scope of the claims.

The invention claimed is:

1. A console for operating an actuating mechanism, the console comprising a controller for operating an actuating mechanism, and a support base for fixing the controller,
  wherein the support base comprises a panel extending in a vertical direction, and an observation platform located below the panel and extending in a horizontal direction, and
  wherein the controller comprises a connecting member, which is connected to the panel and the observation platform respectively,
  characterized in that the connecting member comprises:
    a frustum, of which an axis is perpendicular to a plane where the panel is located; and
    an annular pressure plate fixedly connected to the observation platform, and a fixing collar is provided between the annular pressure plate and the observation platform,
  wherein the panel is provided with a tapered hole, and the frustum is provided in the tapered hole; and
  wherein an axis of the annular pressure plate and an axis of an observation hole on the observation platform coincide with each other.

2. The console for operating an actuating mechanism according to claim 1, characterized in that an inner ring of the annular pressure plate is provided with a mounting groove, and an outer wall of the frustum is connected to a connecting block provided in the mounting groove, wherein the tapered hole is provided with a first opening portion, and the connecting block is provided in the first opening portion.

3. The console for operating an actuating mechanism according to claim 2, characterized in that an outer ring of the annular pressure plate is provided with an extended portion extending in a radial direction of the annular pressure plate, a second opening portion is provided between the panel and the observation platform, and the extended portion is provided in the second opening portion, wherein the first opening portion and the second opening portion are in communication with each other.

4. The console for operating an actuating mechanism according to claim 3, characterized in that the controller further comprises a control handle provided on the frustum), the control handle being a handheld or clamping handle.

5. The console for operating an actuating mechanism according to claim 2, characterized in that the support base is configured to lift up and down on a chassis, a bottom of the chassis is provided with pedals, and the observation hole is used for exposing the pedals to a doctor's field of view.

6. The console for operating an actuating mechanism according to claim 1, characterized in that the support base is configured to lift up and down on a chassis, a bottom of the chassis is provided with pedals, and the observation hole is used for exposing the pedals to a doctor's field of view.

7. The console for operating an actuating mechanism according to claim 1, characterized in that the panel is provided with an emergency operation button, an indicator light, and a speaker.

8. A console for operating an actuating mechanism, the console comprising a controller for operating an actuating mechanism, and a support base for fixing the controller, wherein the support base comprises a panel extending in a vertical direction, and an observation platform located below the panel and extending in a horizontal direction, the support base further comprises a mounting beam and a cantilever, one end of the cantilever being connected to the panel, and the other end of the cantilever being connected to the mounting beam wherein the controller comprises a connecting member, which is connected to the panel and the observation platform respectively, and characterized in that an elbow support platform is further provided on the mounting beam, the elbow support platform and the mounting beam each being configured as an arc-shaped structure, of which an outer side is bent in a direction away from the panel, wherein the elbow support platform and the mounting beam have the same degree of bending.

9. The console for operating an actuating mechanism according to claim 8, characterized in that the panel is provided with an emergency operation button, an indicator light, and a speaker.

10. A console for operating an actuating mechanism, the console comprising a controller for operating an actuating mechanism, and a support base for fixing the controller, wherein the support base comprises a panel extending in a vertical direction, and an observation platform located below the panel and extending in a horizontal direction, and wherein the controller comprises a connecting member, which is connected to the panel and the observation platform respectively, the connecting member comprising a frustum, of which an axis is perpendicular to a plane where the panel is located;

wherein the panel is provided with a tapered hole, and the frustum is provided in the tapered hole; and wherein the support base further comprises a mounting beam and a cantilever, one end of the cantilever being connected to the panel, and the other end of the cantilever being connected to the mounting beam; and characterized in that an elbow support platform is further provided on the mounting beam, the elbow support platform and the mounting beam each being configured as an arc-shaped structure, of which an outer side is bent in a direction away from the panel, wherein the elbow support platform and the mounting beam have the same degree of bending.

11. The console for operating an actuating mechanism according to claim 10, characterized in that the panel is provided with an emergency operation button, an indicator light, and a speaker.

* * * * *